US010492693B2

(12) United States Patent
Irisawa

(10) Patent No.: US 10,492,693 B2
(45) Date of Patent: Dec. 3, 2019

(54) PHOTOACOUSTIC SIGNAL PROCESSING DEVICE, PHOTOACOUSTIC SIGNAL PROCESSING SYSTEM, AND PHOTOACOUSTIC SIGNAL PROCESSING METHOD

(71) Applicant: FUJIFILM Corporation, Tokyo (JP)

(72) Inventor: Kaku Irisawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 440 days.

(21) Appl. No.: 15/220,131

(22) Filed: Jul. 26, 2016

(65) Prior Publication Data

US 2016/0331242 A1 Nov. 17, 2016

Related U.S. Application Data

(63) Continuation of application No. PCT/JP2014/079536, filed on Nov. 7, 2014.

(30) Foreign Application Priority Data

Jan. 27, 2014 (JP) ................................ 2014-012157

(51) Int. Cl.
*A61B 5/00* (2006.01)
*G06T 7/00* (2017.01)
(Continued)

(52) U.S. Cl.
CPC .......... *A61B 5/0095* (2013.01); *A61B 5/0093* (2013.01); *A61B 5/685* (2013.01);
(Continued)

(58) Field of Classification Search
CPC ..... A61B 5/0095; A61B 8/0841; A61B 5/061; A61B 8/4254; A61B 5/6848;
(Continued)

(56) References Cited

U.S. PATENT DOCUMENTS 9,649,034 B2 * 5/2017 Irisawa ................ A61B 5/0095
9,723,995 B2 * 8/2017 Boctor ................. A61B 5/0095
(Continued)

FOREIGN PATENT DOCUMENTS

JP  2005-342128 A  12/2005
JP  2013-511355 A   4/2013

OTHER PUBLICATIONS

Extended European Search Report, dated Jan. 4, 2017, for corresponding European Application No. 14880134.3.
(Continued)

*Primary Examiner* — Amanda Lauritzen Moher
(74) *Attorney, Agent, or Firm* — Birch, Stewart, Kolasch & Birch, LLP

(57) ABSTRACT

Peak specification unit 31 specifies, based on a plurality of photoacoustic-images according to detection signals of photoacoustic-waves detected in a plurality of postures, a photoacoustic-image with the strongest detection signal of a detected photoacoustic-wave among the plurality of photoacoustic-images in a peak search mode. Posture determination unit 32 determines whether or not the posture of the probe 11 at the time of detecting photoacoustic-waves of a generation source of the photoacoustic-image matches the posture of the probe 11 at the time of detecting photoacoustic-waves of a generation source of the photoacoustic-image specified by the peak specification unit in a normal mode. Display control unit 27 displays the photoacoustic image on a display screen, and in a case where the posture determination unit 32 determines that the postures match each other, displays a report indicating the postures matching each other on the display screen.

19 Claims, 9 Drawing Sheets

(51) Int. Cl.
  *A61B 8/00* (2006.01)
  *G10K 15/04* (2006.01)
  *A61B 8/08* (2006.01)
  *A61B 10/02* (2006.01)
  *G01S 7/52* (2006.01)
  *G01S 15/89* (2006.01)
  *A61B 5/06* (2006.01)
  *A61B 34/20* (2016.01)

(52) U.S. Cl.
  CPC .......... *A61B 5/6851* (2013.01); *A61B 5/6852* (2013.01); *A61B 8/0841* (2013.01); *A61B 8/4254* (2013.01); *G06T 7/0012* (2013.01); *G06T 7/0016* (2013.01); *G10K 15/046* (2013.01); *A61B 5/061* (2013.01); *A61B 5/6848* (2013.01); *A61B 8/0833* (2013.01); *A61B 8/4245* (2013.01); *A61B 8/4483* (2013.01); *A61B 8/4494* (2013.01); *A61B 8/463* (2013.01); *A61B 8/5207* (2013.01); *A61B 8/54* (2013.01); *A61B 10/02* (2013.01); *A61B 2034/2063* (2016.02); *G01S 7/52074* (2013.01); *G01S 15/8915* (2013.01)

(58) Field of Classification Search
  CPC ..... A61B 5/6851; A61B 5/685; A61B 5/6852; A61B 8/4483; A61B 2034/2063; G06T 7/0012; G10K 15/046
  See application file for complete search history.

(56) References Cited

U.S. PATENT DOCUMENTS

| 9,974,439 | B2* | 5/2018 | Hirota | A61B 5/0095 |
|---|---|---|---|---|
| 2004/0131299 | A1 | 7/2004 | Adoram et al. | |
| 2007/0238958 | A1* | 10/2007 | Oraevsky | A61B 5/0073 |
| | | | | 600/407 |
| 2008/0262354 | A1* | 10/2008 | Yoshida | A61B 8/469 |
| | | | | 600/443 |
| 2009/0306509 | A1 | 12/2009 | Pedersen et al. | |
| 2010/0249570 | A1* | 9/2010 | Carson | A61B 5/0059 |
| | | | | 600/407 |
| 2010/0268072 | A1* | 10/2010 | Hall | A61N 7/02 |
| | | | | 600/427 |
| 2012/0253200 | A1 | 10/2012 | Stolka et al. | |
| 2012/0285248 | A1* | 11/2012 | Sudo | A61B 5/0095 |
| | | | | 73/602 |
| 2013/0031982 | A1* | 2/2013 | Sato | A61B 5/0095 |
| | | | | 73/655 |
| 2013/0053681 | A1* | 2/2013 | Endo | A61B 8/4245 |
| | | | | 600/411 |
| 2013/0061678 | A1* | 3/2013 | Yamamoto | A61B 5/0095 |
| | | | | 73/602 |
| 2014/0024928 | A1 | 1/2014 | Boctor et al. | |
| 2014/0145648 | A1* | 5/2014 | Tokita | A61B 5/0073 |
| | | | | 315/362 |
| 2015/0327768 | A1* | 11/2015 | Oyama | A61B 5/0095 |
| | | | | 600/407 |
| 2017/0071475 | A1* | 3/2017 | Irisawa | A61B 1/00006 |

OTHER PUBLICATIONS

English Translation of International Preliminary Report on Patentability (including PCT/IB/373 and PCT/ISA/237) for PCT/JP2014/079536, dated Aug. 2, 2016.

International Search Report for PCT/JP2014/079536 dated Dec. 22, 2014.

Written Opinion of the International Searching Authority for PCT/JP2014/079536 dated Dec. 22, 2014.

* cited by examiner

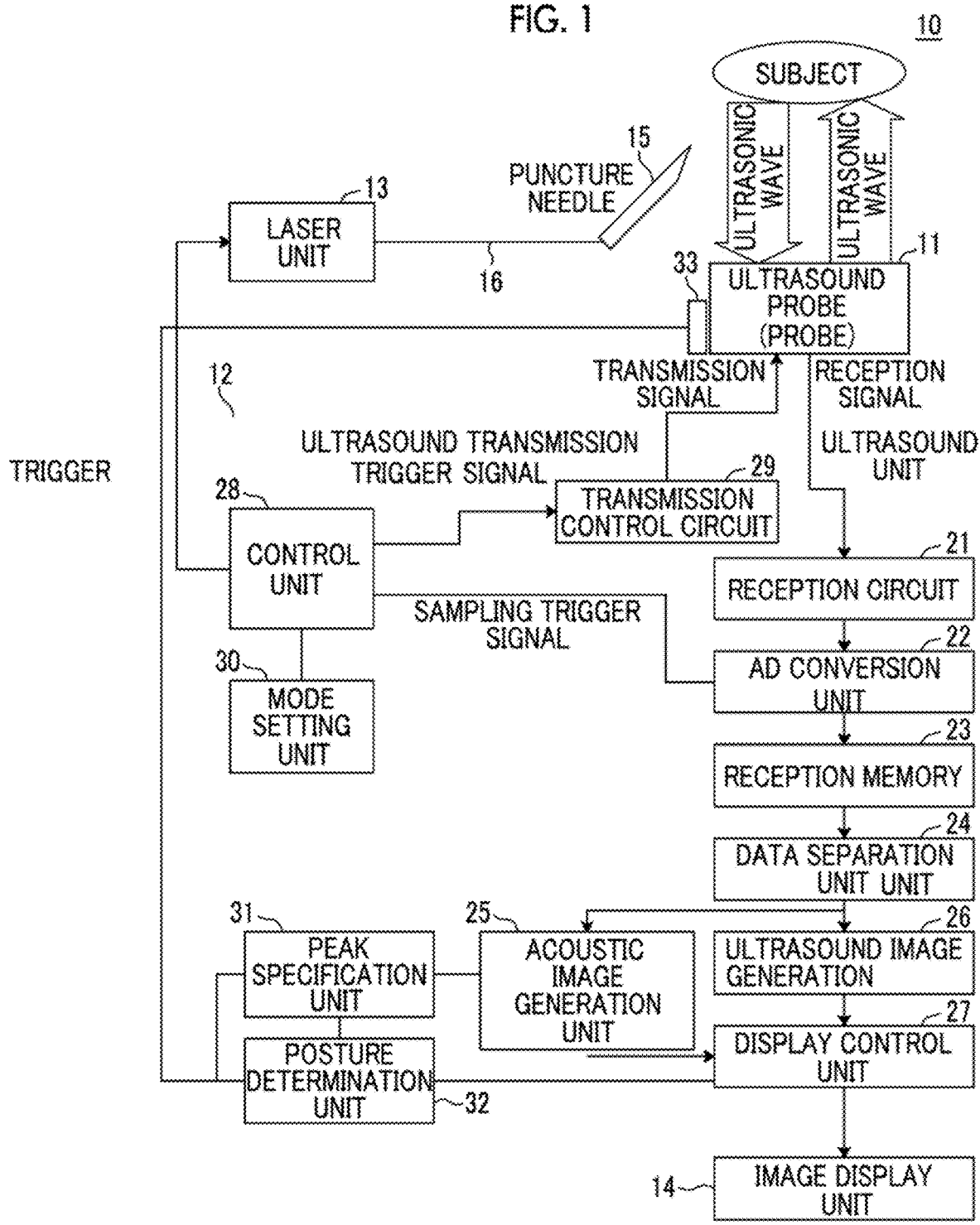

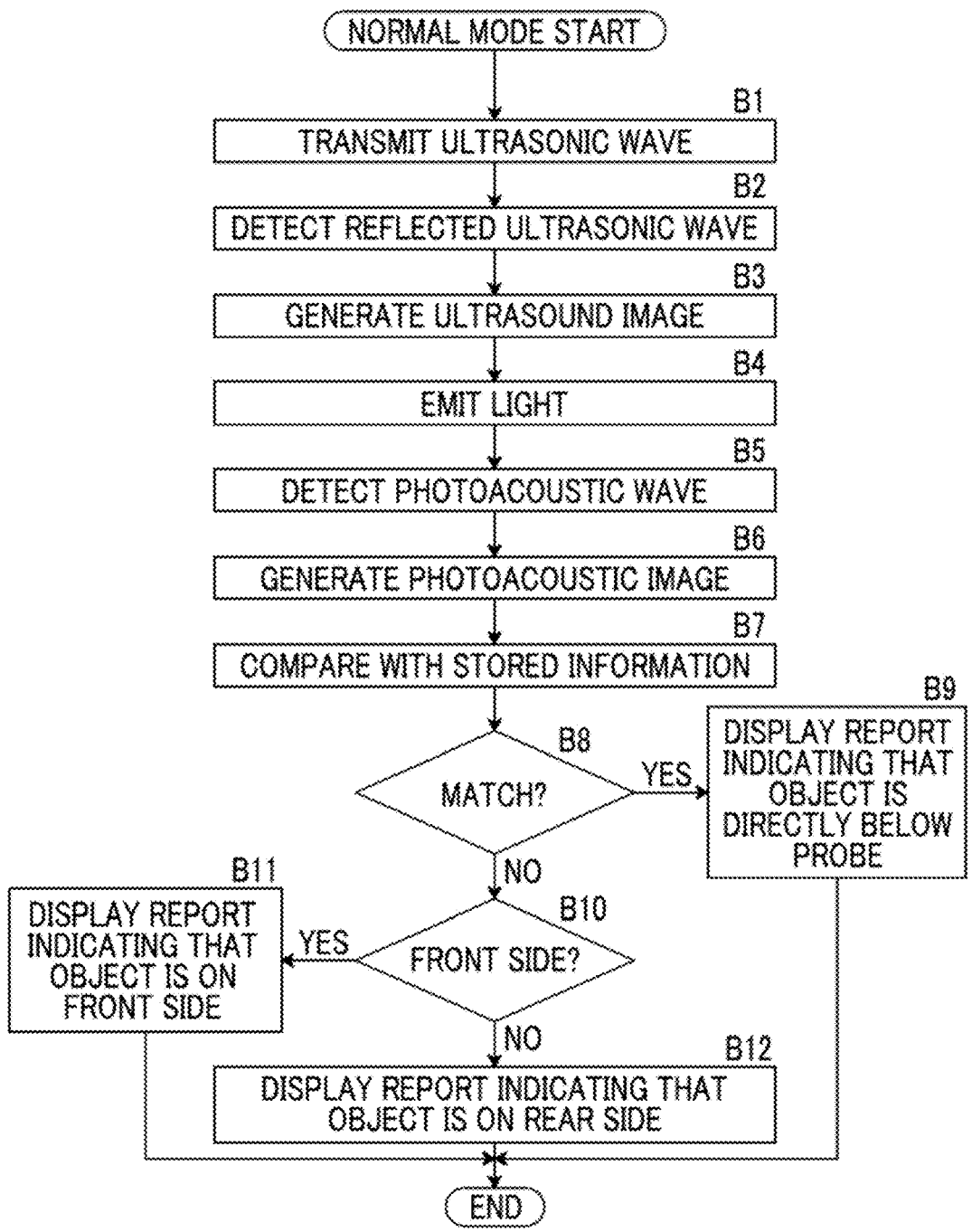

FIG. 10A
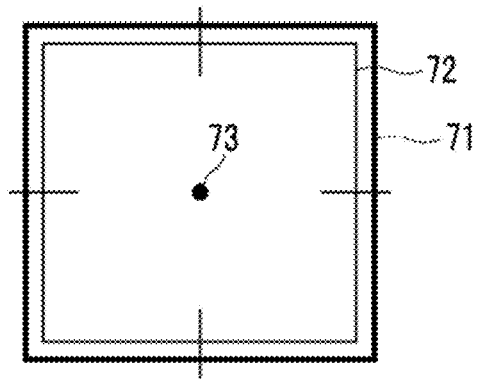
FIG. 10B
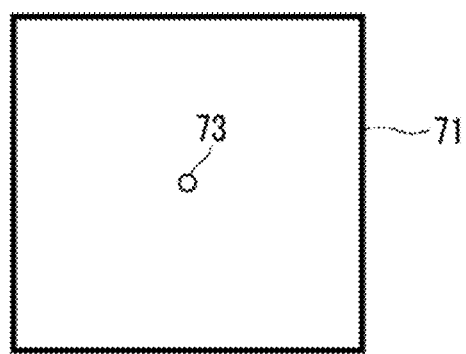
FIG. 11
(A)
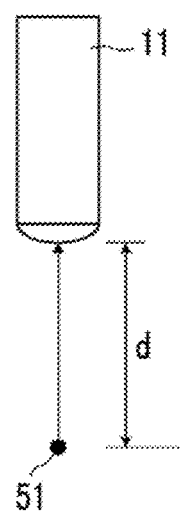
(B)
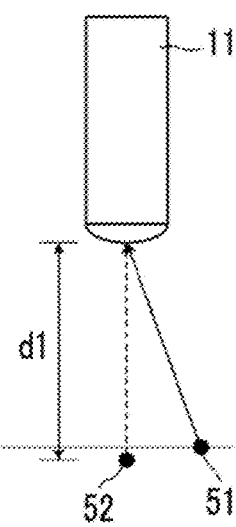

PHOTOACOUSTIC SIGNAL PROCESSING DEVICE, PHOTOACOUSTIC SIGNAL PROCESSING SYSTEM, AND PHOTOACOUSTIC SIGNAL PROCESSING METHOD

CROSS-REFERENCE TO RELATED APPLICATIONS

This application is a Continuation of PCT International Application No. PCT/JP2014/079536 filed on Nov. 7, 2014, which claims priority under 35 U.S.C. § 119(a) to Japanese Patent Application No. 2014-012157 filed on Jan. 27, 2014. Each of the above application(s) is hereby expressly incorporated by reference, in its entirety, into the present application.

BACKGROUND OF THE INVENTION

1. Field of the Invention

The present invention relates to a photoacoustic signal processing device, a photoacoustic signal processing system, and a photoacoustic signal processing method, and particularly, to a photoacoustic signal processing device, a photoacoustic signal processing system, and a photoacoustic signal processing method which detect a photoacoustic wave generated in a subject after light emission to the subject and generate a photoacoustic image.

2. Description of the Related Art

As one image inspection method which can noninvasively inspect a state inside a living body, an ultrasonography method is known. In ultrasonography, an ultrasound (ultrasonic wave) probe which can transmit and receive an ultrasonic wave is used. If an ultrasonic wave is transmitted from the ultrasound probe to the subject (living body), the ultrasonic wave travels inside the living body, and is reflected from a tissue interface. The reflected ultrasonic wave is received by the ultrasound probe, and a distance is calculated based on the time until the reflected ultrasonic wave returns to the ultrasound probe, whereby it is possible to image a status inside the living body.

Furthermore, photoacoustic imaging which images the inside of a living body using a photoacoustic effect is known. In general, in photoacoustic imaging, the inside of the living body is irradiated with a pulse laser beam, such as a laser pulse. Inside the living body, a living body tissue absorbs the energy of the pulse laser beam, and an ultrasonic wave (photoacoustic wave) is generated due to adiabatic expansion caused by the energy of the pulse laser beam. The photoacoustic wave is detected by an ultrasound probe or the like, and a photoacoustic image is constructed based on the detection signal, whereby it is possible to visualize the inside of the living body according to the photoacoustic wave.

JP2005-342128A (Paragraph [0016]) describes that a puncture needle punctured into a subject is imaged by an ultrasound diagnostic apparatus. In general, the puncture needle is made of a metal, such as stainless steel, and the intensity of a reflected ultrasonic wave reflected from the puncture needle is stronger than the intensity of a reflected ultrasonic wave reflected from a living body tissue in the subject, and the presence of the puncture needle on the ultrasound image can be confirmed. In the observation of the puncture needle, it is particularly important to recognize where the tip of the needle is positioned. In JP2005-342128A (Paragraph [0016]), the tip portion of the needle is subjected to special processing for enhancing the reflection of the ultrasonic wave, and the intensity of a reflected ultrasonic wave reflected from the tip portion of the puncture needle is more enhanced than the intensity of a reflected ultrasonic wave reflected from a different portion of the puncture needle.

JP2013-511355A (Paragraph [0096], FIG. 7) describes that a photoacoustic wave is generated from a needle using a photoacoustic effect. In JP2013-511355A (Paragraph [0096], FIG. 7), a pulse laser beam is applied directly to the needle to generate a photoacoustic wave. The needle functions as a wave guide, and the generated photoacoustic wave propagates from a shaft and the tip. The photoacoustic wave emitted from the needle is detected by a probe.

SUMMARY OF THE INVENTION

On the other hand, in ultrasound imaging, an ultrasonic wave (ultrasound beam) transmitted from a probe travels in a straight line at shorter distance and spreads in a spherical shape at longer distance due to the characteristics thereof. In ultrasound imaging, in order to prevent the spread of the ultrasound beam and to improve overall sensitivity, focusing for converging the ultrasound beam is performed. In focusing, for example, an acoustic lens which focuses the ultrasound beam by deflecting the ultrasound beam is used. Since a reflected ultrasonic wave of the transmitted ultrasonic wave is generated in the focused range of the ultrasound beam, an ultrasound image is an image of biological information of a focus plane of the focused ultrasound beam.

In photoacoustic imaging, a photoacoustic wave is generated in a light absorbent in an irradiation range of light. In photoacoustic imaging, unlike ultrasound imaging, the position of the light absorbent as a generation source of a detected photoacoustic wave is not limited to the range of the focused ultrasound beam. A light absorbent outside the range of the focused ultrasound beam generates a photoacoustic wave, and if the photoacoustic wave is detected by the probe, a light absorbent which is not directly below the probe, in other words, on the focus plane of the ultrasound beam focused by the acoustic lens or the like is drawn on the photoacoustic image. For this reason, in a case of recognizing the position of the puncture needle using the photoacoustic image, there is a problem in that, even if the tip of the puncture needle is drawn on the photoacoustic image, it is not determined whether or not the tip of the puncture needle is directly below the probe. This problem occurs even in a case where, instead of the puncture needle, the position of a different inserted object, such as a catheter or a guide wire, inserted into the subject is recognized using a photoacoustic wave generated in the inserted object.

The invention has been accomplished in consideration of the above-described situation, and an object of the invention is to provide a photoacoustic signal processing device, a photoacoustic signal processing system, and a photoacoustic signal processing method which, when recognizing the position of an inserted object inserted into a subject using a photoacoustic image, display the photoacoustic image so as to allow determination of whether or not the inserted object drawn on the photoacoustic image is directly below a probe.

In order to attain the above-described object, the invention provides a photoacoustic signal processing device comprising an acoustic wave detection unit for detecting a photoacoustic wave emitted from an inserted object inserted into a subject, the inserted object having a light guide member configured to guide light from a light source and a photoacoustic wave generation unit configured to absorb light emitted from the light guide member to generate the photoacoustic wave, a photoacoustic image generation unit for generating a photoacoustic image based on a detection signal of the photoacoustic wave, a mode setting unit for setting a peak search mode for detecting the photoacoustic wave in a plurality of postures while changing the posture of the acoustic wave detection unit and a normal mode for displaying the photoacoustic image, a peak specification unit for specifying, based on a plurality of photoacoustic images according to the detection signals of the photoacoustic waves detected in the plurality of postures, a photoacoustic image with the strongest detection signal of the detected photoacoustic wave among the plurality of photoacoustic images in the peak search mode, a posture determination unit for determining whether or not the posture of the acoustic wave detection unit at the time of detecting photoacoustic waves of a generation source of the photoacoustic image matches the posture of the acoustic wave detection unit at the time of detecting photoacoustic waves of a generation source of the photoacoustic image specified by the peak specification unit in the normal mode, and a display control unit for further displaying the photoacoustic image on a display screen, and in a case where the posture determination unit determines that the postures match each other, displaying a report indicating the postures matching each other on the display screen in the normal mode.

The photoacoustic signal processing device of the invention may further comprise a posture detection unit for detecting the angle of the acoustic wave detection unit with respect to a reference direction, the peak specification unit may store the angle of the acoustic wave detection unit at the time of detecting the photoacoustic waves of the generation source of the specified photoacoustic image, and the posture determination unit may compare the stored angle with the angle of the acoustic wave detection unit detected by the posture detection unit at the time of detecting the photoacoustic waves of the generation source of the photoacoustic image to determine whether or not the posture of the acoustic wave detection unit at the time of detecting the photoacoustic waves of the generation source of the photoacoustic image matches the posture of the acoustic wave detection unit at the time of detecting the photoacoustic waves of the generation source of the photoacoustic image specified by the peak specification unit.

The display control unit may display a report indicating the inserted object being shifted in a first direction on the display screen in a case where the angle of the acoustic wave detection unit with respect to the reference direction at the time of detecting the photoacoustic waves of the generation source of the photoacoustic image is greater than the stored angle and may display a report indicating the inserted object being shifted in a second direction opposite to the first direction on the display screen in a case where the angle of the acoustic wave detection unit with respect to the reference direction at the time of detecting the photoacoustic waves of the generation source of the photoacoustic image is smaller than the stored angle.

The posture determination unit may compare the pixel value of the photoacoustic image generated by the photoacoustic image generation unit with the pixel value of the photoacoustic image specified by the peak specification unit to determine whether or not the posture of the acoustic wave detection unit at the time of detecting the photoacoustic waves of the generation source of the photoacoustic image matches the posture of the acoustic wave detection unit at the time of detecting the photoacoustic waves of the generation source of the photoacoustic image specified by the peak specification unit.

The peak specification unit may calculate a maximum value of the pixel values for each of the plurality of photoacoustic images, may compare the calculated maximum values of the pixel values, and may specify a photoacoustic image having a pixel with the largest pixel value as the photoacoustic image with the strongest detection signal of the detected photoacoustic wave.

Instead, the peak specification unit may calculate the total of the pixel values of a plurality of pixels for each of the plurality of photoacoustic images and may determine a photoacoustic image with the largest calculated total of the pixel values as the photoacoustic image with the strongest detection signal of the photoacoustic wave. At this time, the peak specification unit may calculate the total of the pixel values of pixels in a region of interest set in each photoacoustic image.

The peak specification unit may estimate an angle at which the pixel value or the total of the pixel values is maximum based on the relationship between the angle detected by the posture detection unit at the time of detecting the photoacoustic waves of the generation sources of the plurality of photoacoustic images and the maximum value of the pixel values or the total value of the pixel values in each of the plurality of photoacoustic images, may specify a photoacoustic image generated in a case where the photoacoustic wave is detected at the estimated angle as the photoacoustic image with the strongest detection signal of the detected photoacoustic wave, and may store the estimated angle as the angle of the acoustic wave detection unit with the strongest detection signal of the detected photoacoustic wave.

The acoustic wave detection unit may include a plurality of detector elements arranged in a one-dimensional manner, and in the peak search mode, a gradient in a direction orthogonal to the arrangement direction of the detector elements may be changed.

The invention also provides a photoacoustic signal processing system comprising a light source, an inserted object which is inserted into a subject and has a light guide member configured to guide light from the light source and a photoacoustic wave generation unit configured to absorb light emitted from the light guide member and to generate a photoacoustic wave, an acoustic wave detection unit for detecting the photoacoustic wave emitted from the inserted object, a photoacoustic image generation unit for generating a photoacoustic image based on a detection signal of the photoacoustic wave, a mode setting unit for setting a peak search mode for detecting the photoacoustic wave in a plurality of postures while changing the posture of the acoustic wave detection unit and a normal mode for displaying the photoacoustic image, a peak specification unit for specifying, based on a plurality of photoacoustic images according to the detection signals of the photoacoustic waves detected in the plurality of postures, a photoacoustic image with the strongest detection signal of the detected photoacoustic wave among the plurality of photoacoustic images in the peak search mode, a posture determination unit for determining whether or not the posture of the acoustic wave detection unit at the time of detecting photoacoustic waves of a generation source of the photoacoustic image matches the posture of the acoustic wave detection unit at the time of detecting photoacoustic waves of a generation source of the a photoacoustic image specified by the peak specification unit in the normal mode, and display control unit for further displaying the photoacoustic image on a display screen, and in a case where the posture determination unit determines that the postures match each other, displaying a report indicating the postures matching each other in the normal mode.

The invention also provides a photoacoustic signal processing method comprising a step of detecting a photoacoustic wave emitted from an inserted object, which is inserted into a subject and has a light guide member configured to guide light from the light source and a photoacoustic wave generation unit configured to absorb light emitted from the light guide member and to generate a photoacoustic wave, while changing the posture of an acoustic wave detection unit, a step of generating a plurality of photoacoustic images based on detection signals of photoacoustic waves detected in a plurality of postures being changed, a step of specifying a photoacoustic image with the strongest detection signal of the detected photoacoustic wave among the plurality of photoacoustic images based on the plurality of photoacoustic images, a step of detecting the photoacoustic wave emitted from the inserted object, a step of generating a photoacoustic image based on a detection signal of the photoacoustic wave, a step of determining whether or not the posture of the acoustic wave detection unit at the time of detecting the photoacoustic wave matches the posture of the acoustic wave detection unit at the time of detecting photoacoustic waves of a generation source of the specified photoacoustic image, and a step of displaying the photoacoustic image on a display screen, and in a case where it is determined in the determination step that the postures match each other, displaying a report indicating the postures matching each other on the display screen.

In the photoacoustic signal processing device, the photoacoustic signal processing system, and the photoacoustic signal processing method of the invention, it is possible to determine whether or not the inserted object drawn on the photoacoustic image is directly below the probe when recognizing the position of the inserted object inserted into the subject using the photoacoustic image.

BRIEF DESCRIPTION OF THE DRAWINGS

FIG. 1 is a block diagram showing a photoacoustic signal processing system according to a first embodiment of the invention.

FIG. 9 is a flowchart showing an operation procedure in a normal mode.

FIG. 10A is a diagram showing a display example when the tip of the puncture needle is in a directly below direction, FIG. 10B is a diagram showing a display example when the tip of the puncture needle is not in the directly below direction.

Figure 2A:
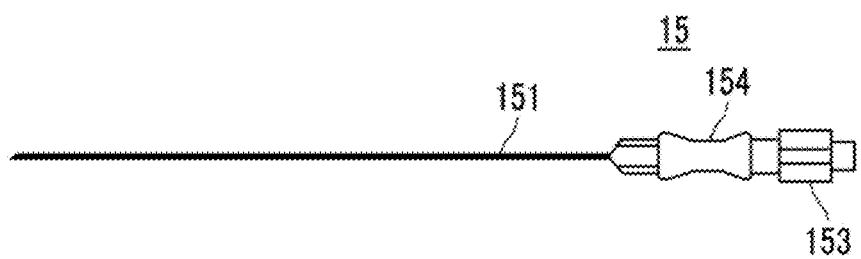
FIG. 2A is a diagram showing the appearance of an entire puncture needle.

(A) of FIG. 11 is a diagram showing a state where the sound source is in the directly below direction, and (B) of FIG. 11 is a diagram showing a state where the sound source is shifted from the directly below direction.

DESCRIPTION OF THE PREFERRED EMBODIMENTS

Hereinafter, an embodiment of the invention will be described in detail referring to the drawings. FIG. 1 shows a photoacoustic signal processing system according to a first embodiment of the invention. A photoacoustic signal processing system 10 includes a probe (ultrasound probe) 11, an ultrasound unit 12, a laser unit 13, and a puncture needle 15. In the embodiment of the invention, although an ultrasonic wave is used as an acoustic wave, the invention is not limited to the ultrasonic wave, and an acoustic wave of an audio frequency may be used if an appropriate frequency is selected according to a target to be inspected, measurement conditions, or the like.

The laser unit 13 as a light source is constituted as, for example, a laser diode light source (semiconductor laser light source). The type of the light source is not particularly limited, and the laser unit 13 may be an optical amplification type laser light source in which a laser diode light source is used as a seed light source. Alternatively, a solid-state laser light source using yttrium-aluminum-garnet (YAG), alexandrite, or the like may be used. A laser beam emitted from the laser unit 13 is guided to the puncture needle 15, for example, using light guide unit, such as an optical fiber 16.

Figure 2B:
FIG. 2B is a diagram showing the appearance of a puncture needle body.
Figure 2C:
FIG. 2C is a diagram showing the appearance of an inner needle.

FIG. 2A shows the appearance of the entire puncture needle, FIG. 2B shows the appearance of a puncture needle body, and FIG. 2C shows the appearance of an inner needle. The puncture needle 15 has a puncture needle body 151 constituting an outer needle and an inner needle 152. The puncture needle body 151 is bonded to an outer needle base 154 (see FIG. 2B), and the inner needle 152 is bonded to an inner needle base 153 (see FIG. 2C). The optical fiber 16 which connects the laser unit 13 (see FIG. 1) and the puncture needle 15 has an optical connector at the tip (on a telescopic end side when viewed from the laser unit 13). The inner needle base 153 of the puncture needle 15 is provided with an optical connector to which the optical connector of the optical fiber 16 is connected.

The puncture needle body 151 has an opening at the tip formed at an acute angle, and has an inner cavity therein. The inner needle 152 has an outer diameter having the substantially same size as the inner cavity of the puncture needle body 151 constituting the outer needle, and is configured to be insertable into the hollow puncture needle body 151. The inner needle 152 is inserted into the inner cavity of the puncture needle body 151 from the outer needle base 154 side, and at least a part of the inner cavity of the puncture needle body 151 is sealed to such an extent that an intercept of a living body is prevented from entering the inner cavity. The inner needle base 153 is provided with a protrusion for connection position alignment, and the outer needle base 154 is provided with a groove which is engaged with the protrusion of the inner needle base 153. When setting the inner needle 152 in the puncture needle body 151, after the positions of the protrusion of the inner needle base 153 and the groove of the outer needle base 154 are aligned with each other, the inner needle base 153 is engaged with the outer needle base 154.

An operator punctures the puncture needle 15 into the subject in a state where the inner needle 152 is set in the puncture needle body 151 (see FIG. 2A). Since the inner cavity of the puncture needle body 151 is closed by the inner needle 152, it is possible to prevent flesh or the like from being caught while the needle is punctured, and to prevent deterioration of an operator's feeling during puncturing the needle. It is also possible to prevent water from flowing into the inner cavity of the puncture needle body 151 from a puncture region. The operator releases the connection between the inner needle base 153 and the outer needle base 154 after puncturing the needle in the subject, and removes the inner needle 152 from the puncture needle body 151. After removing the inner needle 152, the operator mounts a syringe or the like on the outer needle base 154 and injects medicine, such as an anesthetic. Alternatively, the operator samples a biopsy tissue sample from a portion of the subject into which the puncture needle 15 is punctured.

Figure 3:
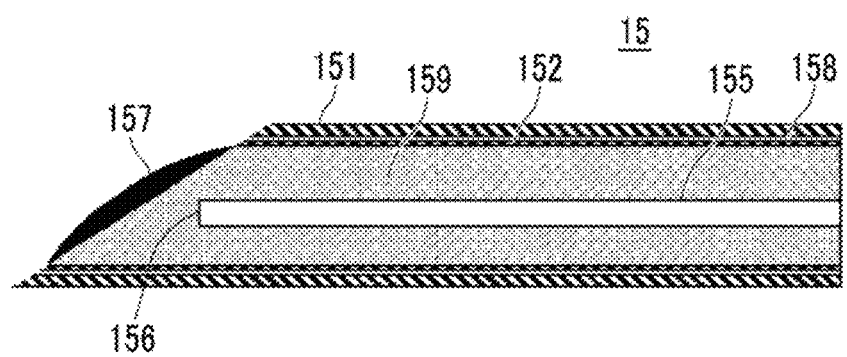
FIG. 3 is a sectional view showing the vicinity of the tip of the puncture needle.

FIG. 3 shows a section in the vicinity of the tip of the puncture needle 15. The inner needle 152 includes a light guide member 155, a light absorption member 157, a tube 158, and transparent resin 159. The tube 158 is a hollow tube which is made of, for example, polyimide. The tube 158 may be a tube made of a metal, such as stainless steel. The outer diameter of the tube 158 is slightly smaller than the diameter of the inner cavity of the puncture needle body 151. The transparent resin 159 is disposed in the tube 158. For example, epoxy resin (adhesive) is used as the transparent resin 159. The tube 158 and the transparent resin 159 are cut at an acute angle like the puncture needle tip formed at an acute angle. The transparent resin 159 has only to close at least the tip portion of the tube 158, and does not necessarily close the entire inside of the tube 158. Photocurable resin, thermosetting resin, or room temperature-curable resin can be used as the transparent resin 159.

Light guided by the optical fiber 16 (see FIG. 1) is incident on the light guide member 155 in the inner needle 152 from the optical connector provided in the inner needle base 153. Instead of providing the optical connector in the inner needle base 153, the optical fiber 16 itself may be used as the light guide member 155. The light guide member 155 guides light emitted from the laser unit 13 near the opening of the puncture needle. Light guided by the light guide member 155 is emitted from a light emission unit 156 provided near the opening. The light guide member 155 is constituted of, for example, an optical fiber, and an end surface of the optical fiber to which light travels when viewed from the laser unit 13 constitutes the light emission unit 156. A laser beam of, for example, 0.2 mJ is emitted from the light emission unit 156.

The light guide member 155 is embedded in the tube 158 by the transparent resin 159. A light absorption member 157 as a photoacoustic wave generation unit is disposed at the tip of the tube 158, and light emitted from the light emission unit 156 is applied to the light absorption member 157. The light absorption member 157 absorbs light to be applied, whereby a photoacoustic wave is generated at the tip of the puncture needle. The light absorption member 157 is at the tip of the puncture needle 15, and a photoacoustic wave can be generated at one point at the tip of the puncture needle 15. The length of a generation source (sound source) of the photoacoustic wave is sufficiently shorter than the length of the entire puncture needle, and the sound source can be considered to be a point sound source. Epoxy resin, polyurethane resin, fluorine resin, silicone rubber, or the like, into which a black pigment is mixed, can be used for the light absorption member 157. Alternatively, a metal film or an oxide film having light absorbency with respect to the wavelength of the laser beam may be used as the light absorption member 157. For example, a film made of an oxide, such as an iron oxide, a chromium oxide, or a manganese oxide, having high light absorbency with respect to the wavelength of the laser beam can be used as the light absorption member 157. Alternatively, a metal film made of Ti, Pt, or the like may be used as the light absorption member 157.

The inner needle 152 described above can be produced by the following procedure. First, the transparent resin 159, which is not yet cured, is injected into the tube 158. Next, the light guide member 155 is inserted into the tube 158, and the light emission end of the light guide member 155 constituting the light emission unit 156 is positioned so as to be disposed near the tip of the tube 158. In positioning, the light guide member 155 is observed using, for example, a microscope or the like, and the position of the light guide member 155 may be adjusted such that the light emission end is disposed at the tip of the tube 158. Since the transparent resin 159 has transparency, it is possible to confirm the position of the light emission end of the light guide member 155 during adjustment. Instead, the light guide member 155 may be inserted first and the transparent resin 159 may be then injected.

After positioning, the transparent resin 159 is cured by, for example, thermal curing in a state where the light guide member 155 is inserted into the tube 158. Thereafter, the tips of the tube 158 and the transparent resin 159 are cut at an acute angle so as to have a shape suitable for the tip of the puncture needle body 151. Subsequently, light-absorbent resin constituting the light absorption member 157 is applied so as to cover at least a part of the cut surfaces, and the resin is cured by, for example, thermal curing.

In the above description, although the light guide member 155 is inserted into the tube 158, the position of the light guide member 155 is adjusted, and the tube is cut at an acute angle after the transparent resin is cured, the invention is not limited thereto. The tube may be cut at an acute angle first, the light guide member 155 may be inserted into the tube, the position of the light guide member 155 may be adjusted, and the transparent resin may be cured. In this case, a metal tube may be used as the tube.

Returning to FIG. 1, the probe 11 is an acoustic wave detection unit, and has, for example, a plurality of ultrasound transducers arranged in a one-dimensional manner. The probe 11 detects a photoacoustic wave generated from the light absorption member 157 (see FIG. 3) after the puncture needle 15 is punctured into the subject. The probe 11 performs transmission of an acoustic wave (ultrasonic wave) to the subject and reception of a reflected acoustic wave (reflected ultrasonic wave) to the transmitted ultrasonic wave, in addition to the detection of the photoacoustic wave. The probe 11 is provided with a posture detection unit 33. For example, an acceleration sensor, an angular velocity sensor, or a gravitational acceleration sensor is used as the posture detection unit 33. The posture detection unit 33 detects the angle of the probe 11 with respect to a reference direction at the time of detecting a photoacoustic wave.

The ultrasound unit 12 has a reception circuit 21, an AD conversion unit 22, reception memory 23, a data separation unit 24, a photoacoustic image generation unit 25, an ultrasound image generation unit 26, a display control unit 27, control unit 28, a transmission control circuit 29, a mode setting unit 30, a peak specification unit 31, and a posture determination unit 32. The probe 11 and the ultrasound unit 12 constitute a photoacoustic signal processing device.

The reception circuit 21 receives a detection signal of a photoacoustic wave detected by the probe 11. Furthermore, the reception circuit 21 receives a detection signal of a reflected ultrasonic wave detected by the probe 11. The AD conversion unit 22 converts the detection signals of the photoacoustic wave and the reflected ultrasonic wave received by the reception circuit 21 to digital signals. The AD conversion unit 22 samples the detection signals of the photoacoustic wave and the reflected ultrasonic wave in a predetermined sampling period based on, for example, a sampling clock signal having a predetermined period. The AD conversion unit 22 stores the sampled detection signals (sampling data) of the photoacoustic wave and the reflected ultrasonic wave in the reception memory 23.

The data separation unit 24 separates sampling data of the detection signal of the photoacoustic wave stored in the reception memory 23 from sampling data of the detection signal of the reflected ultrasonic wave. The data separation unit 24 inputs sampling data of the detection signal of the photoacoustic wave to the photoacoustic image generation unit 25. Furthermore, the data separation unit 24 inputs separated sampling data of the reflected ultrasonic wave to the ultrasound image generation unit (reflected acoustic image generation unit) 26.

The photoacoustic image generation unit 25 generates a photoacoustic image based on the detection signal of the photoacoustic wave detected by the probe 11. The generation of the photoacoustic image includes, for example, image reconstruction, such as phase matching addition, detection, logarithmic conversion, and the like. The ultrasound image generation unit 26 generates an ultrasound image (reflected acoustic image) based on the detection signal of the reflected ultrasonic wave detected by the probe 11. The generation of the ultrasound image also includes image reconstruction, such as phase matching addition, detection, logarithmic conversion, and the like.

The control unit 28 controls the respective units of the ultrasound unit 12. For example, the control unit 28 sends a trigger signal to the laser unit 13 to cause a laser beam to be emitted from the laser unit 13. Furthermore, the control unit 28 sends a sampling trigger signal to the AD conversion unit 22 according to the application of the laser beam to control the sampling start timing of the photoacoustic wave.

In a case of acquiring an ultrasound image, the control unit 28 sends an ultrasound transmission trigger signal which instructs the transmission control circuit 29 to perform ultrasound transmission. If the ultrasound transmission trigger signal is received, the transmission control circuit 29 causes an ultrasonic wave to be transmitted from the probe 11. The control unit 28 sends a sampling trigger signal to the AD conversion unit 22 according to the timing of ultrasound transmission and starts the sampling of the reflected ultrasonic wave.

The mode setting unit 30 sets an operation mode of the ultrasound unit 12. The operation mode includes a peak search mode for detecting a photoacoustic wave in a plurality of postures while changing the posture of the probe 11 and a normal mode for performing normal display of a photoacoustic image. When the operation mode is the peak search mode, while the user is changing the postures of the probe 11, the control unit 28 causes light emission and detection of a photoacoustic wave to be carried out multiple times. The photoacoustic image generation unit 25 generates a plurality of photoacoustic images based on the detection signals of the photoacoustic waves detected in a plurality of postures. The peak specification unit 31 specifies a photoacoustic image with the strongest detection signal of the detected photoacoustic wave among a plurality of generated photoacoustic images. The peak specification unit 31 stores the angle of the probe 11 at the time of detecting the photoacoustic waves of the generation source of the specified photoacoustic image with the strongest detection signal of the detected photoacoustic wave.

The posture determination unit 32 determines whether or not the posture of the probe 11 at the time of detecting the photoacoustic waves of the generation source of the photoacoustic image generated by the photoacoustic image generation unit 25 matches the posture of the probe 11 at the time of detecting the photoacoustic waves of the generation source of the photoacoustic image specified by the peak specification unit when the operation mode is the normal mode. For example, the posture determination unit 32 compares the angle stored in the peak specification unit 31 with the angle of the probe 11 detected by the posture detection unit 33 at the time of detecting the photoacoustic waves of the generation source of the photoacoustic image to determine whether or not the posture of the probe 11 at the time of detecting the photoacoustic waves of the generation source of the photoacoustic image matches the posture of the probe 11 at the time of detecting the photoacoustic waves of the generation source of the photoacoustic image specified by the peak specification unit 31. Both postures do not necessarily completely match each other, and if the difference is within a predetermined range, for example, a range of about ±10%, it may be considered that both postures match each other.

The display control unit 27 composes the photoacoustic image and the ultrasound image and displays a composite image on the image display unit 14, such as a display, in the normal mode. For example, the display control unit 27 performs image composition by superimposing the photoacoustic image and the ultrasound image. When the posture determination unit 32 determines that both postures match each other, the display control unit 27 displays a report indicating both postures matching each other on the image display unit. In this embodiment, the "normal mode" means a mode in which the specification of the photoacoustic image with the strongest detection signal of the detected photoacoustic wave by the peak specification unit 31 is not carried out. When the operation mode is the peak search mode, the specification of the photoacoustic image with the strongest detection signal of the detected photoacoustic wave may be performed while performing the generation of the ultrasound image and the display of the composite image, and image display may be omitted.

Figure 4A:
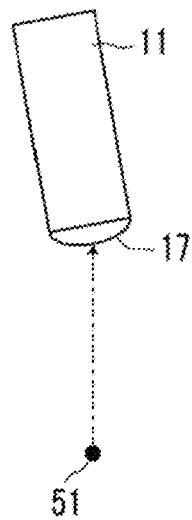
FIGS. 4A to 4C are diagrams showing detection of a photoacoustic wave when the posture of a probe is changed.
Figure 4B:
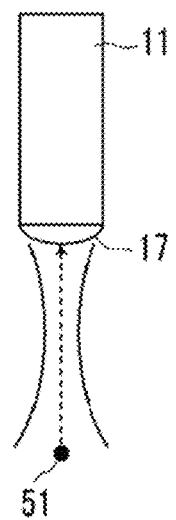
Figure 4C:
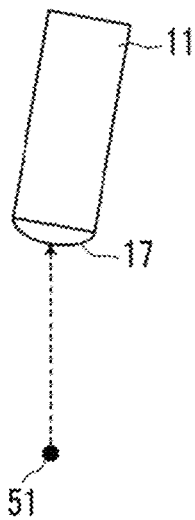

FIGS. 4A to 4C show detection of a photoacoustic wave when the posture of the probe 11 is changed. The angle which is detected by the posture detection unit 33 when the probe 11 is in a posture of FIG. 4B is defined as 0°. A sign in a gradient direction of the probe 11 shown in FIG. 4A is set as positive, and a sign in a gradient direction of the probe 11 shown in FIG. 4B is set as negative. The probe 11 has an acoustic lens 17 which focuses an ultrasound beam, and an imaging cross-section of an ultrasound image matches a focus plane of the focused ultrasound beam. Hereinafter, the direction of the focus plane of the focused ultrasound beam is defined as a direction directly below the probe 11.

In FIG. 4B, a sound source 51 is directly below the probe 11. If the probe 11 is inclined as shown in FIG. 4A or 4C, the sound source 51 is shifted from the directly below direction of the probe 11. However, even in this case, the detector elements of the probe 11 can detect photoacoustic waves generated from the sound source 51, and the sound source 51 is drawn on a photoacoustic image. Since the probe 11 detects the photoacoustic waves even when the sound source 51 is not in the directly below direction, it is difficult to determine whether the tip of the puncture needle 15 as a sound source is in the directly below direction of the probe 11 or in a direction slightly shifted from this direction only by observing the photoacoustic image.

The photoacoustic wave detection characteristic of the probe 11 has angle dependence, and a detection signal of a photoacoustic wave obliquely incident on a detection surface of the acoustic wave becomes weaker than a detection signal of a photoacoustic wave incident perpendicularly to the detection surface. Accordingly, when the sound source 51 is directly below the probe 11, the detected photoacoustic wave becomes the strongest. Accordingly, in this embodiment, in the peak search mode, the detection of the photoacoustic wave is performed while changing the posture of the probe 11, and the photoacoustic image with the strongest detection signal of the detected photoacoustic wave among a plurality of photoacoustic images based on a plurality of photoacoustic waves detected in a plurality of postures is specified. The posture of the probe 11 at the time of detecting the photoacoustic waves to be the generation source of the photoacoustic image specified by the peak specification unit 31 matches the posture in which the sound source 51 is directly below the probe 11.

For example, the peak specification unit 31 compares the pixel values among a plurality of photoacoustic images and specifies the photoacoustic image with the strongest detection signal of the detected photoacoustic wave. In more detail, the peak specification unit 31 first calculates the maximum value of the pixel values in the image for each of a plurality of photoacoustic images. Next, the calculated maximum values of the pixel values are compared with each other. The peak specification unit 31 specifies a photoacoustic image having a pixel with the largest pixel value among a plurality of photoacoustic images as the photoacoustic image with the strongest detection signal of the detected photoacoustic wave. The peak specification unit 31 stores the angle detected by the posture detection unit 33 at the time of detecting the photoacoustic waves of the generation source of the specified photoacoustic image as the angle when the sound source 51 is directly below the probe 11.

Instead, the peak specification unit 31 may calculate the total of the pixel values of a plurality of pixels for each of a plurality of photoacoustic images and may compare the calculated totals of the pixel values. For example, the peak specification unit 31 calculates the total of the pixel values of all pixels included in the photoacoustic image. The peak specification unit 31 specifies a photoacoustic image with the largest total of the pixel values as the photoacoustic image with the strongest detection signal of the detected photoacoustic wave. The peak specification unit 31 stores the angle detected by the posture detection unit 33 at the time of detecting the photoacoustic waves of the generation source of the specified photoacoustic image as the angle when the sound source 51 is directly below the probe 11.

Instead of calculating the total of the pixel values of the entire image, a region of interest may be set in the photoacoustic image, and the total of the pixel values of the pixels in the set region of interest may be calculated. The region of interest is designated on the photoacoustic image by the user, for example, when switching to the peak search mode. Alternatively, a position where the detection signal of the detected photoacoustic wave in the image is the strongest may be recognized as the position of the needle tip, and a predetermined range from the position of the needle tip may be set as a region of interest. In a case of calculating the total of the pixel values in the region of interest, even when there are many artifacts, it is possible to accurately specify the photoacoustic image with the strongest detection signal of the detected photoacoustic wave.

The peak specification unit 31 may estimate an angle, at which the pixel value or the total of the pixel values is the largest, based on the relationship between the angle detected by the posture detection unit 33 at the time of detecting the photoacoustic waves of the generation sources of a plurality of photoacoustic images and the maximum value of the pixel values or the total value of the pixel values in each of a plurality of photoacoustic images, and may specify a photoacoustic image generated when a photoacoustic wave is detected at the estimated angle as the photoacoustic image with the strongest detection signal of the detected photoacoustic wave. In more detail, the peak specification unit 31 plots the angle of the probe 11 at the time of detecting the photoacoustic wave and the maximum value of the pixel values of each photoacoustic image or the total value of the pixel values of a plurality of pixels and performs fitting using a least-squares method with a Gaussian function to calculate the angle at which the maximum value of the pixel values or the total value of the pixel values is the largest. The peak specification unit 31 may store the estimated angle as the angle when the sound source 51 is directly below the probe 11.

In the normal mode, the posture of the probe 11 is compared with the posture of the probe 11 at the time of detecting the photoacoustic waves to be the generation source of the specified photoacoustic image, whereby it is possible to determine whether or not the sound source 51 drawn on the photoacoustic image is directly below the probe 11. If the posture determination unit 32 determines that the postures of the probe 11 match each other, the display control unit 27 displays a report indicating the sound source 51 being directly below the probe on the image display unit 14.

When the posture determination unit 32 determines that the postures of the probe 11 do not match each other, the display control unit 27 displays a report indicating the sound source 51 being not directly below the probe 11. In more detail, as shown in FIG. 4A, when the angle of the probe 11 is greater than the angle when the sound source is directly below the probe 11, the display control unit 27 displays a report indicating the sound source 51 being shifted in a first direction (in FIG. 4A, a left direction toward the paper) from the focus plane of the acoustic lens 17. Conversely, as shown in FIG. 4C, when the angle of the probe 11 is smaller than the angle when the sound source is directly below the probe 11, the display control unit 27 displays a report indicating the sound source 51 being shifted in a second direction (in FIG. 4C, a right direction toward the paper) from the focus plane of the acoustic lens 17.

Figure 5:
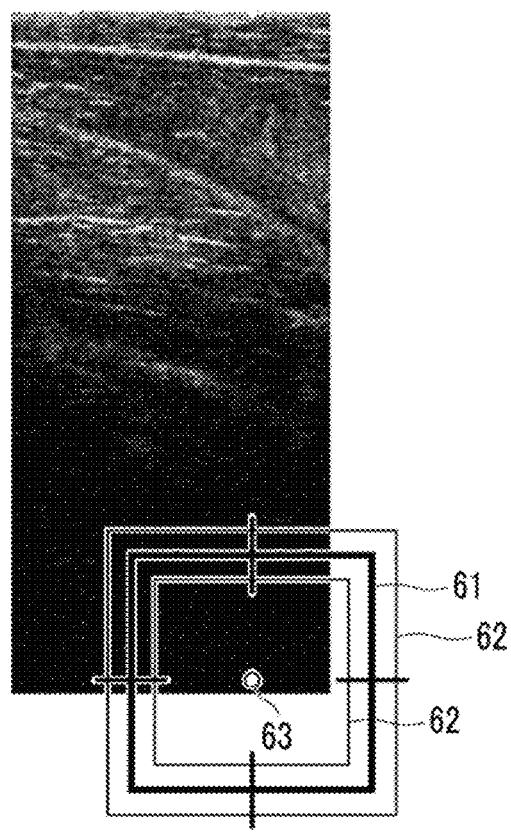
FIG. 5 shows an image display example when a sound source is directly below the probe.

FIG. 5 shows an image display example when the sound source is directly below the probe 11. The display control unit 27 overlaps a frame 61 and a sound source position 63 with the composite image of the photoacoustic image and the ultrasound image. The sound source position 63 is displayed in a pixel corresponding to a position where a detection signal of a photoacoustic wave is present in an image, and the frame 61 is displayed at the position where the center thereof matches the sound source position 63. When the posture determination unit 32 determines that the postures of the probe 11 match each other, the display control unit 27 displays rectangles 62 respectively inside and outside the frame 61. The user, such as a physician, visually recognizes that the rectangles 62 are displayed respectively inside and outside the frame 61, thereby recognizing that the tip of the puncture needle as a sound source is directly below the probe 11.

Figure 6:
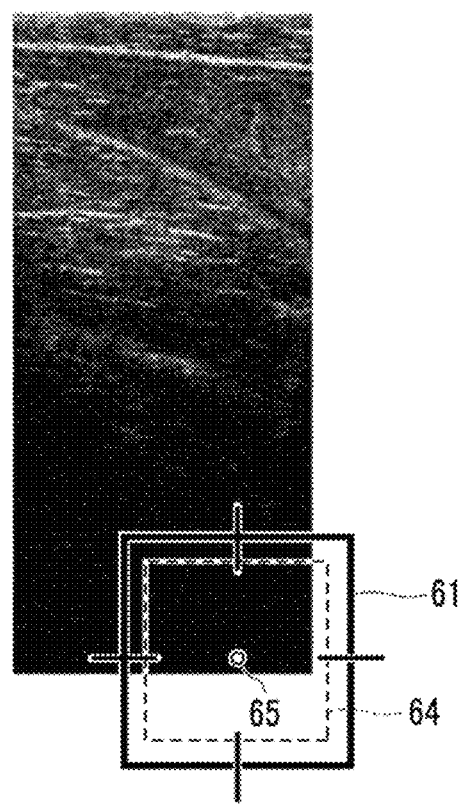
FIG. 6 shows an image display example when the sound source is shifted in a first direction.

FIG. 6 shows an image display example when the sound source is shifted in the first direction. The display control unit 27 overlaps a frame 61 and a sound source position 65 with the composite image of the photoacoustic image and the ultrasound image. When the posture determination unit 32 determines that the angle of the probe 11 is greater than the angle when the sound source is directly below the probe 11 (see FIG. 4A), the display control unit 27 displays a rectangle 64 only inside the frame 61. The rectangle 64 is displayed by, for example, a broken line. The user, such as a physician, visually recognizes that the rectangle 64 is displayed only inside the frame 61, thereby recognizing that the tip of the puncture needle as a sound source is shifted fin the first direction from the directly below direction of the probe 11.

Figure 7:
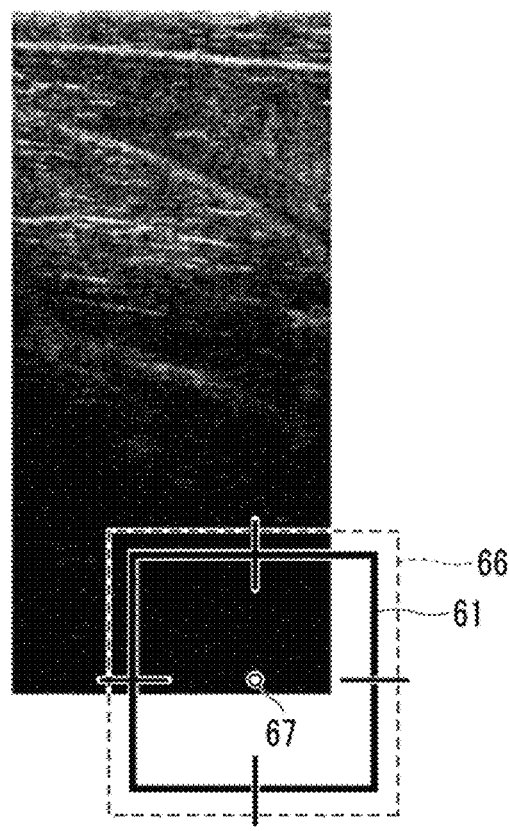
FIG. 7 shows an image display example when the sound source is shifted in a second direction.

FIG. 7 shows an image display example when the sound source is shifted in the second direction. The display control unit 27 overlaps a frame 61 and a sound source position 67 with the composite image of the photoacoustic image and the ultrasound image. When the posture determination unit 32 determines that the angle of the probe 11 is smaller than the angle when the sound source is directly below the probe 11 (see FIG. 4C), the display control unit 27 displays a rectangle 66 only outside the frame 61. The rectangle 66 is displayed by, for example, a broken line. The user, such as a physician, visually recognizes that the rectangle 66 is displayed only outside the frame 61, thereby recognizing that the tip of the puncture needle as a sound source is shifted in the second direction from the directly below direction of the probe 11.

Figure 8:
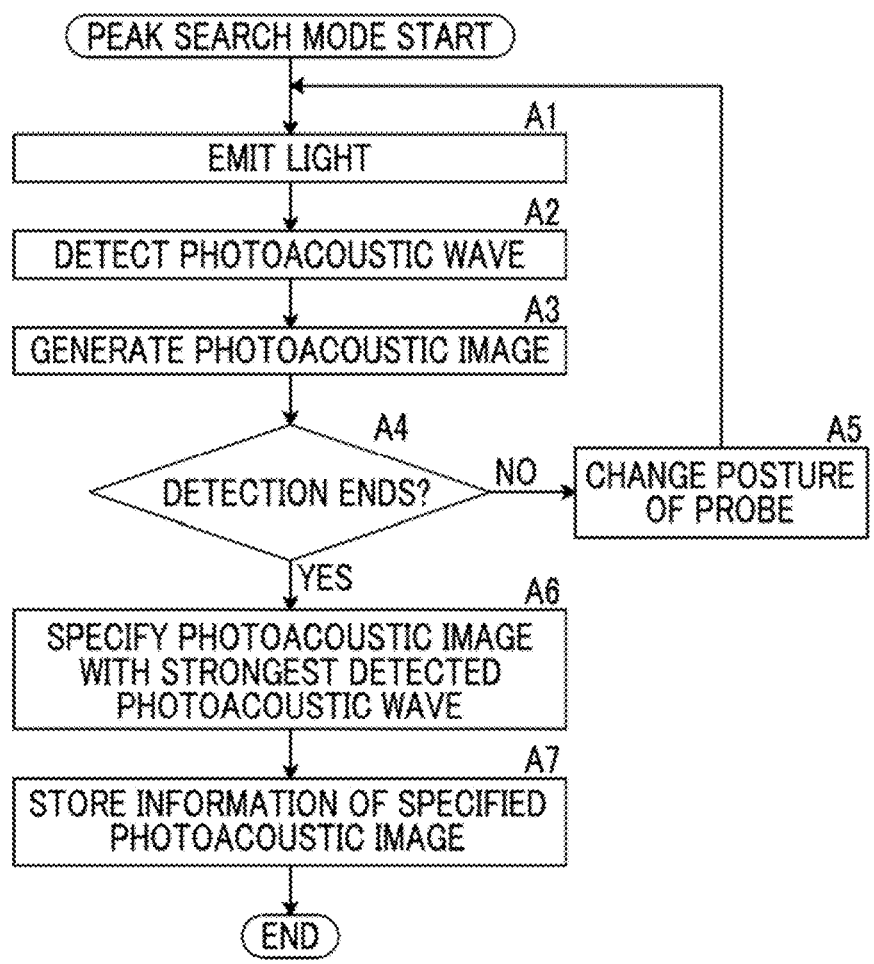
FIG. 8 is a flowchart showing an operation procedure of a peak search mode.

FIG. 8 shows an operation procedure of the peak search mode. The user, such as a physician, punctures the puncture needle 15 into the subject. The mode setting unit 30 sets the operation mode to the peak search mode. For example, the user operates a mode selection switch to set the operation mode to the peak search mode. Alternatively, a swinging operation of the probe 11 by the user may be detected and the operation mode may be automatically set to the peak search mode.

The control unit 28 of the ultrasound unit 12 sends the trigger signal to the laser unit 13. If the trigger signal is received, the laser unit 13 starts laser oscillation and emits a pulse laser beam (Step A1). The pulse laser beam emitted from the laser unit 13 is guided near the tip of the puncture needle 15 by the light guide member 155 (see FIG. 3) and is emitted from the light emission unit 156, and at least a part of the pulse laser beam is applied to the light absorption member 157 disposed at the tip of the puncture needle 15.

The probe 11 detects a photoacoustic wave generated in the subject with the application of the laser beam (Step A2). The AD conversion unit 22 receives the detection signal of the photoacoustic wave through the reception circuit 21, samples the detection signal of the photoacoustic wave, and stores the detection signal of the photoacoustic wave in the reception memory 23. The data separation unit 24 transmits the detection signal of the photoacoustic wave stored in the reception memory 23 to the photoacoustic image generation unit 25. The photoacoustic image generation unit 25 generates a photoacoustic image based on the detection signal of the photoacoustic wave (Step A3).

The control unit 28 determines whether or not a detection end condition is satisfied (Step A4). For example, the control unit 28 determines whether or not the photoacoustic wave is detected in a plurality of postures. For example, when the angle of the probe 11 is changed in a range of ±20°, it is determined that the detection end condition is satisfied. Alternatively, it is determined whether or not a predetermined time, for example, several seconds, have elapsed from the start of detection. In addition, when the gradient of the probe is changed in a given direction, and when it is detected that the intensity of the detection signal of the photoacoustic wave is turned from an increase to a decrease with respect to the change in gradient, detection may end. The user may instruct to end detection. In a case where the detection end condition is not satisfied, for example, the user changes the gradient in a direction orthogonal to the arrangement direction of the detector elements of the probe 11 (Step A5). Thereafter, the process returns to Step A1. The control unit 28 causes light emission, detection of a photoacoustic wave, and generation of a photoacoustic image to be performed until the detection end condition is satisfied.

If the detection end condition is satisfied, the peak specification unit 31 specifies the photoacoustic image with the strongest detection signal of the detected photoacoustic wave among a plurality of photoacoustic images based on a plurality of photoacoustic waves detected in a plurality of postures (Step A6). The peak specification unit 31 stores information relating to the posture of the probe 11 at the time of detecting the photoacoustic waves of the generation source of the specified photoacoustic image (Step A7). For example, the peak specification unit 31 stores the angle of the probe 11 detected by the posture detection unit 33 at the time of detecting the photoacoustic waves of the generation source of the specified photoacoustic image as information relating to the posture of the probe 11. If information relating to the posture of the probe 11 at the time of detecting the photoacoustic waves of the generation source of the specified photoacoustic image is stored, the peak search mode ends.

FIG. 9 shows an operation procedure in the normal mode. If the peak search mode ends, the mode setting unit 30 sets the operation mode to the normal mode. The control unit 28 of the ultrasound unit 12 sends the ultrasound transmission signal to the transmission control circuit 29. The transmission control circuit 29 causes an ultrasonic wave to be transmitted from the probe 11 in response to the ultrasound transmission trigger signal (Step B1). The probe 11 detects a reflected ultrasonic wave after the transmission of the ultrasonic wave (Step B2). The transmission and reception of the ultrasonic wave may be performed at positions separated from each other. For example, the transmission of the ultrasonic wave may be performed at a position different from the probe 11, and the reflected ultrasonic wave to the transmitted ultrasonic wave may be received by the probe 11.

The reflected ultrasonic wave detected by the probe 11 is input to the AD conversion unit 22 through the reception circuit 21. The AD conversion unit 22 samples the detection signal of the reflected ultrasonic wave and stores the detection signal of the reflected ultrasonic wave in the reception memory 23. The data separation unit 24 transmits the detection signal of the reflected ultrasonic wave stored in the reception memory 23 to the ultrasound image generation unit 26. The ultrasound image generation unit 26 generates an ultrasound image based on the detection signal of the reflected ultrasonic wave (Step B3).

The control unit 28 sends the trigger signal to the laser unit 13. If the trigger signal is received, the laser unit 13 starts laser oscillation and emits a pulse laser beam (Step B4). The pulse laser beam emitted from the laser unit 13 is guided near the tip of the puncture needle 15 by the light guide member 155 (see FIG. 3) and is emitted from the light emission unit 156, and at least a part of the pulse laser beam is applied to the light absorption member 157 disposed at the tip of the puncture needle 15.

The probe 11 detects a photoacoustic wave generated in the subject with the application of the laser beam, that is, the photoacoustic wave emitted from the light absorption member 157 (Step B5). The AD conversion unit 22 receives a detection signal of the photoacoustic wave through the reception circuit 21, samples the detection signal of the photoacoustic wave, and stores the detection signal of the photoacoustic wave in the reception memory 23. The data separation unit 24 transmits the detection signal of the photoacoustic wave stored in the reception memory 23 to the photoacoustic image generation unit 25. The photoacoustic image generation unit 25 generates a photoacoustic image based on the detection signal of the photoacoustic wave (Step B6).

While the reflected ultrasonic wave transmitted from the probe 11 propagates between the probe 11 and an ultrasonic wave reflection position in a reciprocating manner, the photoacoustic wave propagates through one way from the vicinity of the tip of the puncture needle 15 as the generation position of the photoacoustic wave to the probe 11. Accordingly, the detection of the reflected ultrasonic wave requires the time two times longer than the detection of the photoacoustic wave generated at the same depth position. For this reason, the sampling clock of the AD conversion unit 22 at the time of sampling the reflected ultrasonic wave may be half the sampling clock at the time of sampling the photoacoustic wave.

The posture determination unit 32 compares information relating to the posture of the probe 11 stored in Step A7 (see FIG. 8) of the peak search mode in the peak specification unit 31 with the posture of the probe 11 at the time of detecting the photoacoustic wave (Step B7), and determines whether or not both postures match each other (Step B8). When both postures match each other, the posture determination unit 32 transmits a signal indicating the tip of the puncture needle 15 being directly below the probe 11 to the display control unit 27. The display control unit 27 displays the composite image of the ultrasound image and the photoacoustic image on the image display unit 14, and displays the report indicating the tip of the puncture needle 15 being directly below the probe 11 on the image display unit 14 (Step B9). In Step B9, for example, the image shown in FIG. 5 is displayed.

When it is determined that both postures of the probe 11 do not match each other, the posture determination unit 32 determines whether or not the tip of the puncture needle 15 is on the front side (first direction) (Step B10). For example, the posture determination unit 32 compares the magnitude relationship between the angle of the probe 11 detected by the posture detection unit 33 and the angle of the probe 11 stored in the peak specification unit 31, and if the angle of the probe 11 detected by the posture detection unit 33 is greater than the angle of the probe 11 stored in the peak specification unit 31 (the difference is positive), determines that the tip of the puncture needle 15 is on the front side from the directly below direction of the probe 11. In this case, the posture determination unit 32 transmits a signal indicating the tip of the puncture needle 15 being on the front side to the display control unit 27. The display control unit 27 displays the composite image of the ultrasound image and the photoacoustic image on the image display unit 14, and displays the report indicating the tip of the puncture needle 15 being on the front side on the image display unit 14 (Step B11). In Step B11, for example, the image shown in FIG. 6 is displayed.

For example, the posture determination unit 32 compares the magnitude relationship between the angle of the probe 11 detected by the posture detection unit 33 and the angle of the probe 11 stored in the peak specification unit 31, and if the angle of the probe 11 detected by the posture detection unit 33 is smaller than the angle of the probe 11 stored in the peak specification unit 31 (the difference is negative), in Step B10, determines that the tip of the puncture needle 15 is on the rear side from the directly below direction of the probe 11. In this case, the posture determination unit 32 transmits a signal indicating the tip of the puncture needle 15 being on the rear side to the display control unit 27. The display control unit 27 displays the composite image of the ultrasound image and the photoacoustic image on the image display unit 14, and displays the report indicating the tip of the puncture needle 15 being on the rear side on the image display unit 14 (Step B12). In Step B12, for example, the image shown in FIG. 7 is displayed.

In this embodiment, in the peak search mode, a plurality of photoacoustic images are generated based on the photoacoustic waves detected while changing the posture of the probe 11, and the photoacoustic image with the strongest detection signal of the detected photoacoustic wave is specified. In the normal mode, it is determined whether or not the posture of the probe 11 at the time of detecting the photoacoustic waves matches the posture of the probe 11 at the time of detecting the photoacoustic waves of the generation source of the photoacoustic image specified in the peak search mode. When the tip of the puncture needle 15 as a sound source is directly below the probe 11, the detection signal of the detected photoacoustic wave is the strongest; thus, when detecting the photoacoustic wave in a posture matching the posture of the probe 11 at this time, it can be estimated that the tip of the puncture needle is directly below the probe 11. Accordingly, in this embodiment, it is possible to display the photoacoustic image so as to allow determination of whether or not the inserted object drawn on the photoacoustic image is directly below the probe when recognizing the position of the inserted object inserted into the subject using the photoacoustic image.

In the comparison with JP2005-342128A (Paragraph [0016]), since the needle is drawn as a continuous body in the ultrasound image, the recognition of the tip portion is difficult. In order to extract the needle tip using the ultrasound image, special processing for enhancing the reflected ultrasonic wave reflected from the needle tip portion is required, and this affects cost or puncture capacity. Furthermore, in JP2013-511355A (Paragraph [0096], FIG. 7), since the photoacoustic wave is generated from the entire needle, the needle is drawn as a continuous body, and the recognition of the tip portion is difficult. In this embodiment, the photoacoustic wave is generated in a narrower range when it is more considered to be a point sound source, and the recognition of the needle tip is easy. However, since the photoacoustic wave generated in the needle tip portion can be detected even in a case where the needle tip portion is not directly below the probe 11, even if a point sound source is on an image, the point sound source is not necessarily directly below the probe 11. In this embodiment, in the peak search mode, the posture of the probe 11 in which the strongest detection signal of the photoacoustic wave is detected is specified, and in the normal mode, it is determined whether or not the posture of the probe 11 matches the specified posture. In this way, it is possible to determine whether or not a point sound source drawn on an image is directly below the probe 11.

Next, a second embodiment of the invention will be described. In the first embodiment, in the peak search mode, the photoacoustic image with the strongest detection signal of the detected photoacoustic wave is specified, and the posture of the probe 11 at the time of detecting the photoacoustic waves of the generation source of the photoacoustic image is stored. In the normal mode, the posture of the probe 11 detected by the posture detection unit 33 is compared with the posture of the probe 11 stored in the peak search mode to determine whether or not the tip of the puncture needle 15 as a sound source is directly below the probe 11. In this embodiment, in the peak search mode, the photoacoustic image with the strongest detection signal of the detected photoacoustic wave is specified, and in the normal mode, the pixel value of the photoacoustic image is compared with the pixel value of the photoacoustic image specified in the peak search mode to determine whether or not the tip of the puncture needle 15 as a sound source is directly below the probe 11. Other parts may be the same as those in the first embodiment.

As in the first embodiment, the peak specification unit 31 specifies the photoacoustic image with the strongest detection signal of the detected photoacoustic wave. The peak specification unit 31 stores the pixel value in the specified photoacoustic image, instead of storing the posture of the probe 11 at the time of detecting the photoacoustic waves of the generation source of the specified photoacoustic image. In a case where the photoacoustic image with the strongest detection signal of the detected photoacoustic wave is specified based on the maximum pixel value in each image, the peak specification unit 31 stores the maximum pixel value in the specified photoacoustic image. In a case where the photoacoustic image with the strongest detection signal of the detected photoacoustic wave is specified based on the total value of the pixel values of the entire image, the peak specification unit 31 stores the total value of the pixel values of the entire specified image. In a case where the photoacoustic image with the strongest detection signal of the detected photoacoustic wave is specified based on the total value of the pixel values of the region of interest in the image, the peak specification unit 31 stores the total value of the pixel values of the region of interest in the specified photoacoustic image.

The posture determination unit 32 compares the pixel value of the photoacoustic image generated by the photoacoustic image generation unit 25 with the pixel value or the total value stored in the peak specification unit in the peak search mode to determine whether or not the posture of the probe 11 at the time of detecting the photoacoustic waves of the generation source of the photoacoustic image matches the posture of the probe 11 at the time of detecting the photoacoustic waves of the generation source of the photoacoustic image specified by the peak specification unit 31 in the normal mode. The photoacoustic wave detected by the probe 11 is the largest when the tip of the puncture needle 15 is directly below the probe 11, and accordingly, the pixel value of the photoacoustic image becomes the maximum; thus, the pixel values or the total pixel values of a plurality of pixels are compared with each other, whereby it is possible to determine whether or not the tip of the puncture needle 15 is directly below the probe 11.

FIG. 10A shows a display example when the tip of the puncture needle 15 is directly below the probe 11, and FIG. 10B shows a display example when the tip of the puncture needle 15 is not directly below the probe 11. When the pixel values or the total values of the pixel values match each other, the posture determination unit 32 transmits a signal indicating the tip of the puncture needle 15 being directly below the probe 11 to the display control unit 27. In this case, the display control unit 27 displays a frame 71, a sight 72, and a sound source position 73 shown in FIG. 10A so as to overlap the composite of the photoacoustic image and the ultrasound image. The sound source position 73 is displayed in a pixel corresponding to a position where a photoacoustic wave is present in an image, and the frame 71 and the sight 72 are displayed at positions where the center thereof matches the sound source position 73.

When the pixel values or the total values of the pixel values do not match each other, the posture determination unit 32 transmits a signal indicating the tip of the puncture needle 15 being not directly below the probe 11 to the display control unit 27. In this case, the display control unit 27 displays a frame 71 and a sound source position 73 shown in FIG. 10B so as to overlap the composite image of the photoacoustic image and the ultrasound image. The user, such as a physician, can determine whether or not the tip of the puncture needle as a sound source is directly below the probe 11 according to the presence or absence of the sight 72 (see FIG. 10A).

In this embodiment, in the peak search mode, a plurality of photoacoustic images are generated based on the photoacoustic waves detected while changing the posture of the probe 11, and the photoacoustic image with the strongest detection signal of the detected photoacoustic wave is specified. In the normal mode, it is determined whether or not the pixel value or the total value of the pixel values in the photoacoustic image matches the pixel value or the total value of the pixel values of the photoacoustic image specified in the peak search mode. The pixel values are compared with each other in this way, whereby it is possible to display the photoacoustic image so as to allow determination of whether or not the inserted object drawn on the photoacoustic image is directly below the probe when recognizing the position of the inserted object inserted into the subject using the photoacoustic image. In this embodiment, it is determined whether or not the tip of the puncture needle 15 is directly below the probe 11 based on the pixel value, and since it is not necessary to compare the postures of the probe 11 at the time of detecting the photoacoustic waves, the posture detection unit 33 is not required.

Subsequently, a third embodiment of the invention will be described. In this embodiment, the photoacoustic waves are detected while changing the position in the space of the probe 11, instead of detecting the photoacoustic waves while changing the gradient of the probe 11. The peak specification unit 31 specifies a photoacoustic image generated when the tip of the puncture needle 15 is directly below the probe 11 based on the position in the depth direction of the sound source in a plurality of photoacoustic images generated based on the photoacoustic waves detected while changing the position. When the position in the depth direction of the sound source in the photoacoustic image matches the position in the depth direction of the sound source in the photoacoustic image specified by the peak specification unit 31, the posture determination unit 32 determines that the tip of the puncture needle 15 is directly below the probe 11. Other parts may be the same as those in the first embodiment or the second embodiment.

(A) of FIG. 11 shows a state where the sound source is directly below the probe 11, and (B) of FIG. 11 shows a state where the sound source is shifted from the directly below direction. The distance between the sound source 51 as the tip of the puncture needle and the probe 11 is represented by d (see (A) of FIG. 11). When the sound source 51 is directly below the probe 11, the sound source 51 is drawn at the position at the depth d in the photoacoustic image. If the position of the probe 11 is slightly shifted from the position shown in (A) of FIG. 11 in the left direction of the paper as shown in (B) of FIG. 11, the position of the probe 11 is shifted, whereby the distance between the probe 11 and the sound source 51 becomes longer than the distance d. When the detection of the photoacoustic waves is performed in the state of (B) of FIG. 11, a sound source position 52 in the photoacoustic image becomes d1 which is deeper than the depth d in a case where the sound source 51 is directly below the probe 11.

As above, the position in the depth direction of the sound source in the photoacoustic image becomes the minimum when the sound source 51 is directly below the probe 11. The peak specification unit 31 specifies a photoacoustic image with the shallowest sound source position among a plurality of photoacoustic images generated based on the photoacoustic waves detected while changing the position. If the angle dependence of the photoacoustic wave detection characteristics of the detector elements of the probe 11 is also considered, the photoacoustic image with the shallowest sound source position in the depth position corresponds to the photoacoustic image with the strongest detection signal of the detected photoacoustic wave. The posture determination unit 32 determines whether or not the position in the depth direction of the sound source in the photoacoustic image matches the position in the depth direction of the sound source in the photoacoustic image specified by the peak specification unit 31, thereby determining whether or not the tip of the puncture needle 15 is directly below the probe 11.

In this embodiment, in the peak search mode, a plurality of photoacoustic images are generated based on the photoacoustic waves detected while changing the position of the probe 11, and the photoacoustic image in which the position in the depth direction of the drawn sound source is the shallowest is specified. In the normal mode, it is determined whether or not the position in the depth direction of the sound source in the photoacoustic image matches the position in the depth direction of the sound source in the photoacoustic image specified in the peak search mode. The positions in the depth direction of the sound source in the images are compared with each other, whereby it is also possible to display the photoacoustic image so as to allow determination of whether or not the inserted object drawn on the photoacoustic image is directly below the probe when recognizing the position of the inserted object inserted into the subject using the photoacoustic image.

In the respective embodiments described above, although the figures displayed on the image are changed between when the tip of the puncture needle 15 is directly below the probe 11 and when the tip of the puncture needle 15 is not directly below the probe 11 (see FIGS. 5 to 7, 10A and 10B), the invention is not limited thereto. Image display may be performed if the user is taught about whether or not the tip of the puncture needle 15 is directly below the probe 11, and for example, an indicator indicating that the tip of the puncture needle 15 is directly below the probe 11 may be merely displayed in a display image. Alternatively, the same figure may be displayed when the tip of the puncture needle 15 is directly below the probe 11 and when the tip of the puncture needle 15 is not directly below the probe 11, and the display luminance or display color of the figure may be changed.

In the first embodiment, position detection unit for detecting the position in the space of the probe 11 may be used to detect the position of the probe 11 in the space, in addition to the angle of the probe 11. In this case, the position in the space of the tip of the puncture needle 15 as a sound source may be determined based on the angle and position of the probe 11. In the normal mode, when the position of the probe 11 is shifted from the position in the peak search mode, it may be determined whether the tip of the puncture needle 15 is shifted in the first direction or in the second direction from the directly below direction of the probe 11 based on the relationship between the position of the tip of the puncture needle 15 and a current imaging cross-section.

In FIG. 3, although an example where the light guide member 155 is embedded in the tube 158 using the transparent resin 159, and the light absorption member 157 is disposed at the tip of the transparent resin 159 has been described, the invention is not limited thereto. For example, a light-absorbent film may be used as the light absorption member 157, the light emission unit 156 as the light emission surface of the light guide member 155 may be covered with the light-absorbent film, and the light guide member 155 may be embedded in the transparent resin. Alternatively, a gap may be provided between the light emission unit 156 of the light guide member 155 and the light absorption member 157, and the light emission unit 156 and the light absorption member 157 may face each other through an air layer.

In FIG. 3, although an example where the inner needle 152 has the tube 158 has been described, the invention is not limited thereto. For example, the inner needle may be made of a light-absorbent material, for example, black resin, and the light guide member 155 may be embedded in the inner needle. In this case, the inner needle, in particular, the tip portion thereof also serves as the light absorption member 157 which absorbs light emitted from the light emission unit 156 of the light guide member 155 to generate an acoustic wave. Instead of embedding the light guide member 155 in the resin, the light guide member 155 having the substantially same outer diameter as the inner diameter of the puncture needle body 151 may be used, and the light guide member 155 itself may be used as the inner needle. In this case, a light-absorbent film, for example, black fluorine resin may be used as the light absorption member 157, and at least a part of the light guide member 155 including the light emission unit 156 may be covered with, for example, the black fluorine rein.

In the first embodiment, although an example where the puncture needle 15 has the puncture needle body 151 constituting the outer needle and the inner needle 152 has been described, the inner needle 152 is not required. In a case where the puncture needle 15 has no inner needle, the light guide member 155 may be inserted into the inner cavity of the puncture needle body 151, and the light absorption member 157 may be provided at a position of the inner wall of the puncture needle body 151, to which light emitted from the light emission unit 156 is applied. The light absorption member 157 may also serve as a fixing member which fixes the tip portion of the light guide member 155 to the inner cavity of the puncture needle body 151. The light guide member 155, such as an optical fiber, may be fixed to the inner wall in the inner cavity of the inserted object, such as the puncture needle, using an adhesive. Alternatively, a hollow tube having a diameter smaller than that of the inner cavity may be inserted into the inner cavity of the inserted object, and the light guide member 155 may be fixed by the tube.

The light absorption member 157 is not required. For example, light emitted from the light emission unit 156 may be applied to the puncture needle body 151, and a portion of the puncture needle body 151 applied with light may be used as a photoacoustic wave generation unit, and a photoacoustic wave may be generated from this portion. For example, the light emission unit and the photoacoustic wave generation unit may be disposed in the vicinity of the tip of the puncture needle 15, and a photoacoustic wave may be generated in the vicinity of the tip of the puncture needle 15. The vicinity of the tip of the puncture needle 15 means a position where, in a case where the light emission unit and the photoacoustic wave generation unit are disposed at this position, a photoacoustic wave capable of imaging the position of the tip of the puncture needle 15 can be generated with accuracy necessary for a puncture operation. For example, the vicinity of the tip of the puncture needle 15 indicates a range of 0 mm to 3 mm from the tip of the puncture needle 15 toward the base.

The puncture needle 15 is not limited to a puncture needle which is punctured into the subject from the outside of the subject percutaneously, and may be a needle for an ultrasound endoscope. The light guide member 155 and the light absorption member 157 may be provided in the needle for an ultrasound endoscope, light is applied to the light absorption member 157 provided in the needle tip portion, and a photoacoustic wave may be detected to generate a photoacoustic image. In this case, the needle for an ultrasound endoscope can be punctured while observing the photoacoustic image to confirm the position of the tip portion of the needle for an ultrasound endoscope. A photoacoustic wave generated in the tip portion of the needle for an ultrasound endoscope may be detected using a probe for a body surface or may be detected by a probe assembled in an endoscope.

In the respective embodiments described above, although the puncture needle 15 is considered as the inserted object, the invention is not limited thereto. The inserted object may be a radiofrequency cauterization needle which houses electrodes for use in radiofrequency cauterization, may be a catheter which is inserted into a blood vessel, or may be a guide wire of a catheter which is inserted into a blood vessel. Alternatively, the inserted object may be an optical fiber for laser treatment.

In the respective embodiments described above, although a needle having an opening at the tip thereof is assumed as the needle, the opening is not necessarily provided at the tip portion of the needle. The needle is not limited to a needle, such as an injection needle, and may be a biopsy needle for use in biopsy. That is, the needle may be a biopsy needle which is punctured into an inspection object of a living body and can sample the tissue of a biopsy region of the inspection object. In this case, a photoacoustic wave may be generated in a sampler (suction port) which is used to sample the tissue of a biopsy region by suction. Furthermore, the needle may be used as a guide needle which is used for the insertion of a needle to a deep portion, such as an organ under the skin or in the abdominal cavity.

Although the invention has been described based on the preferred embodiment, the photoacoustic signal processing device, system, and method of the invention are not limited to the foregoing embodiments, and various alterations may be carried out from the configurations of the foregoing embodiments and may fall within the scope of the invention.

EXPLANATION OF REFERENCES

10: photoacoustic signal processing system
11: probe
12: ultrasound unit
13: laser unit
14: image display unit
15: puncture needle
16: optical fiber
17: acoustic lens
21: reception circuit
22: AD conversion unit
23: reception memory
24: data separation unit
25: photoacoustic image generation unit
26: ultrasound image generation unit
27: display control unit
28: control unit
29: transmission control circuit
30: mode setting unit
31: peak specification unit
32: posture determination unit
33: posture detection unit
51: sound source
52: sound source on image
61: frame
62, 64, 66: rectangle
63, 65, 67: sound source position
71: frame
72: sight
73: sound source position
151: puncture needle body (outer needle)
152: inner needle
153: inner needle base
154: outer needle base
155: light guide member
156: light emission unit
157: light absorption member
158: tube
159: transparent resin

What is claimed is:

1. A photoacoustic signal processing system comprising:
a light source;
an inserted object which is adapted to be inserted into a subject and has a light guide configured to guide light from the light source and a light absorber configured to absorb light emitted from the light guide and to generate a photoacoustic wave;
a probe that detects the photoacoustic wave emitted from the inserted object; and
a processor configured to:
  generate a photoacoustic image based on a detection signal of the photoacoustic wave;
  set a peak search mode for detecting the photoacoustic wave in a plurality of postures while the posture of the probe is changing and a normal mode for displaying the photoacoustic image;
  select, based on a plurality of photoacoustic images based on the detection signals of the photoacoustic waves detected in the plurality of postures, a photoacoustic image with the strongest detection signal of the detected photoacoustic wave among the plurality of photoacoustic images in the peak search mode;
  determine whether or not a posture of the probe at the time of detecting photoacoustic waves associated with the photoacoustic image matches a posture of the probe at the time of detecting photoacoustic waves associated with the photoacoustic image specified by the processor in the normal mode; and
  display the photoacoustic image on a display screen, and in a case where the processor determines that the postures match each other, displaying a report indicating the postures matching each other in the normal mode.

2. The photoacoustic signal processing system according to claim 1, wherein the processor calculates a maximum value of pixel values for each of the plurality of photoacoustic images, compares the calculated maximum values of the pixel values, and specifies a photoacoustic image having a pixel with the largest pixel value as the photoacoustic image with the strongest detection signal of the detected photoacoustic wave.

3. The photoacoustic signal processing system according to claim 1, further comprising:
a posture detection sensor that detects an angle of the probe with respect to a reference direction,
wherein the processor stores an angle of the probe at the time of detecting the photoacoustic waves associated with the specified photoacoustic image, and
the processor compares the stored angle with the angle of the probe detected by the posture detection sensor at the time of detecting the photoacoustic waves associated with the photoacoustic image to determine whether or not the posture of the probe at the time of detecting the photoacoustic waves associated with the photoacoustic image matches the posture of the probe at the time of detecting the photoacoustic waves associated with the photoacoustic image specified by the processor.

4. The photoacoustic signal processing system according to claim 1, wherein the probe includes a plurality of detector elements arranged in a one-dimensional manner, and
in the peak search mode, a gradient of the probe in a direction orthogonal to the arrangement direction of the detector elements is changed.

5. The photoacoustic signal processing system according to claim 3, wherein the processor estimates an angle at which the pixel value or the total of the pixel values is maximum based on the relationship between the angle detected by the posture detection sensor at the time of detecting the photoacoustic waves associated with the plurality of photoacoustic images and the maximum value of the pixel values or the total value of the pixel values in each of the plurality of photoacoustic images, specifies a photoacoustic image generated in a case where the photoacoustic wave is detected at the estimated angle as the photoacoustic image with the strongest detection signal of the detected photoacoustic wave, and stores the estimated angle as the angle of the probe with the strongest detection signal of the detected photoacoustic wave.

6. The photoacoustic signal processing system according to claim 3, wherein the processor displays a report indicating the inserted object being shifted in a first direction on the display screen in a case where the angle of the probe with respect to the reference direction at the time of detecting the photoacoustic waves associated with the photoacoustic image is greater than the stored angle and displays a report indicating the inserted object being shifted in a second direction opposite to the first direction on the display screen in a case where the angle of the probe with respect to the reference direction at the time of detecting the photoacoustic waves associated with the photoacoustic image is smaller than the stored angle.

7. The photoacoustic signal processing system according to claim 6, wherein the processor calculates a maximum value of pixel values for each of the plurality of photoacoustic images, compares the calculated maximum values of the pixel values, and specifies a photoacoustic image having a pixel with the largest pixel value as the photoacoustic image with the strongest detection signal of the detected photoacoustic wave.

8. The photoacoustic signal processing system according to claim 6, wherein the processor estimates an angle at which the pixel value or the the pixel values is maximum based on the relationship between the angle detected by the posture detection sensor at the time of detecting the photoacoustic waves associated with the plurality of photoacoustic images and the maximum value of the pixel values or the total value of the pixel values in each of the plurality of photoacoustic images, specifies a photoacoustic image generated in a case where the photoacoustic wave is detected at the estimated angle as the photoacoustic image with the strongest detection signal of the detected photoacoustic wave, and stores the estimated angle as the angle of the probe with the strongest detection signal of the detected photoacoustic wave.

9. The photoacoustic signal processing system according to claim 6, wherein the processor calculates a total of pixel values of a plurality of pixels for each of the plurality of photoacoustic images and determines a photoacoustic image with the largest calculated total of the pixel values as the photoacoustic image with the strongest detection signal of the photoacoustic wave.

10. The photoacoustic signal processing system according to claim 9, wherein the processor calculates a total of pixel values of pixels in a region of interest set in each photoacoustic image.

11. The photoacoustic signal processing system according to claim 3, wherein the processor calculates a maximum value of pixel values for each of the plurality of photoacoustic images, compares the calculated maximum values of the pixel values, and specifies a photoacoustic image having a pixel with the largest pixel value as the photoacoustic image with the strongest detection signal of the detected photoacoustic wave.

12. The photoacoustic signal processing system according to claim 3, wherein the processor calculates a total of pixel values of a plurality of pixels for each of the plurality of photoacoustic images and determines a photoacoustic image with the largest calculated total of the pixel values as the photoacoustic image with the strongest detection signal of the photoacoustic wave.

13. The photoacoustic signal processing system according to claim 12, wherein the processor calculates a total of pixel values of pixels in a region of interest set in each photoacoustic image.

14. The photoacoustic signal processing system according to claim 3, wherein the probe includes a plurality of detector elements arranged in a one-dimensional manner, and
in the peak search mode, a gradient of the probe in a direction orthogonal to the arrangement direction of the detector elements is changed.

15. The photoacoustic signal processing device system according to claim 1, wherein the processor compares a pixel value of the photoacoustic image generated by the processor with a pixel value of the photoacoustic image specified by the processor to determine whether or not the posture of the probe at the time of detecting the photoacoustic waves associated with the photoacoustic image matches the posture of the probe at the time of detecting the photoacoustic waves associated with the photoacoustic image specified by the processor.

16. The photoacoustic signal processing system according to claim 15, wherein the processor calculates a maximum value of pixel values for each of the plurality of photoacoustic images, compares the calculated maximum values of the pixel values, and specifies a photoacoustic image having a pixel with the largest pixel value as the photoacoustic image with the strongest detection signal of the detected photoacoustic wave.

17. The photoacoustic signal processing system according to claim 1, wherein the processor calculates a total of pixel values of a plurality of pixels for each of the plurality of photoacoustic images and determines a photoacoustic image with the largest calculated total of the pixel values as the photoacoustic image with the strongest detection signal of the photoacoustic wave.

18. The photoacoustic signal processing system according to claim 17, wherein the processor calculates a total of pixel values of pixels in a region of interest set in each photoacoustic image.

19. A photoacoustic signal processing method using the photoacoustic signal processing system according to claim 1 comprising:
   detecting the photoacoustic wave emitted from the inserted object, which is inserted into the subject and has the light guide configured to guide light from the light source and the light absorber configured to absorb light emitted from the light guide and to generate the photoacoustic wave, in a plurality of postures of the probe;
   generating the plurality of photoacoustic images based on detection signals of photoacoustic waves detected in the plurality of postures being changed;
   specifying the photoacoustic image with the strongest detection signal of the detected photoacoustic wave among the plurality of photoacoustic images;
   detecting the photoacoustic wave emitted from the inserted object;
   generating the photoacoustic image based on a detection signal of the photoacoustic wave;
   determining whether or not the posture of the probe at the time of detecting the photoacoustic wave matches the posture of the probe at the time of detecting photoacoustic waves associated with the specified photoacoustic image; and
   displaying the photoacoustic image on the display screen, and in a case where it is determined in the determination step that the postures match each other, displaying the report indicating the postures matching each other on the display screen.

\* \* \* \* \*